(12) United States Patent
Allen et al.

(10) Patent No.: US 8,409,066 B2
(45) Date of Patent: Apr. 2, 2013

(54) METHOD AND APPARATUS FOR FOLDING A WEB

(75) Inventors: Kyle Solomon Allen, Neenah, WI (US); David Arthur Trefethren, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1186 days.

(21) Appl. No.: 11/496,131

(22) Filed: Jul. 31, 2006

(65) Prior Publication Data

US 2008/0026925 A1    Jan. 31, 2008

(51) Int. Cl.
*B31F 1/10* (2006.01)
(52) U.S. Cl. .................. 493/423; 493/427; 493/441
(58) Field of Classification Search ........... 493/419, 493/423, 424, 427, 441, 442
See application file for complete search history.

(56) References Cited

U.S. PATENT DOCUMENTS

| | | | |
|---|---|---|---|
| 3,661,680 A * | 5/1972 | Gore | 156/467 |
| 3,828,367 A * | 8/1974 | Bourgeois | 2/402 |
| 4,420,148 A | 12/1983 | Meadows | |
| 4,650,530 A * | 3/1987 | Mahoney et al. | 156/73.1 |
| 4,663,220 A | 5/1987 | Wisneski et al. | |
| 4,704,116 A | 11/1987 | Enloe | |
| 5,046,272 A | 9/1991 | Vogt et al. | |
| 5,226,992 A | 7/1993 | Morman | |
| 6,192,521 B1 | 2/2001 | Alberts et al. | |
| 6,315,022 B1 * | 11/2001 | Herrin et al. | 156/459 |
| 6,358,350 B1 | 3/2002 | Glaug et al. | |
| 6,482,278 B1 * | 11/2002 | McCabe et al. | 156/73.1 |
| 6,585,840 B2 | 7/2003 | Rabe et al. | |
| 2002/0174930 A1 * | 11/2002 | Umebayashi et al. | 156/62.6 |
| 2003/0216705 A1 | 11/2003 | Coates | |
| 2003/0217803 A1 | 11/2003 | Hermansson et al. | |
| 2004/0060648 A1 | 4/2004 | Thorson et al. | |
| 2004/0108043 A1 | 6/2004 | Otsubo | |
| 2005/0148980 A1 | 7/2005 | Fitton | |
| 2005/0241747 A1 | 11/2005 | Allen | |
| 2005/0241748 A1 | 11/2005 | Allen | |

FOREIGN PATENT DOCUMENTS

| | | |
|---|---|---|
| EP | 0 217 032 B1 | 2/1992 |
| EP | 0 638 505 A1 | 2/1995 |
| EP | 1 108 371 A1 | 6/2001 |
| EP | 1 504 738 A2 | 2/2005 |
| EP | 1 552 798 A1 | 7/2005 |
| WO | WO 01/87217 A2 | 11/2001 |
| WO | WO 01/87218 A2 | 11/2001 |
| WO | WO 01/87562 A2 | 11/2001 |
| WO | WO 01/87753 A2 | 11/2001 |
| WO | WO 01/88245 A2 | 11/2001 |
| WO | WO 02/49565 A2 | 6/2002 |
| WO | WO 2004/073430 A2 | 9/2004 |

\* cited by examiner

*Primary Examiner* — Thanh Truong
(74) *Attorney, Agent, or Firm* — R. Joseph Foster, III; David J. Arteman

(57) ABSTRACT

A web has a series of cut outs that define bridging portions therebetween. A method for folding the web includes providing the web to a first conveyor, folding the web about a folding wheel to define a folded edge that extends through the series of cut outs, transferring the web to a second conveyor having an included angle of 15 to 40 degrees in relation to the first conveyor, folding the web about a folding bar to maintain the folded edge, and spanning at least one cut out with the folding bar and contemporaneously contacting at least two bridge portions with the folding bar to maintain the folded edge of the web about the folding bar as the web passes the folding wheel edge.

12 Claims, 8 Drawing Sheets

METHOD AND APPARATUS FOR FOLDING A WEB

BACKGROUND OF THE INVENTION

Various methods of folding webs are known in the art. For example, folding boards, folding bars, vacuum folders, and the like, and combinations thereof have been used in various converting operations such as disposable absorbent article manufacturing. However, as disposable absorbent articles have become more "garment-like" the manufacturing processes, including the folding processes, have become more complex. For example, the folding processes may include folding webs having multiple layers of material, discrete attachments, cut away portions, and the like, and combinations thereof. Traditional folding processes are not suited to fold such complex webs. Therefore, there remains a need for a method and apparatus for folding a complex web during high-speed converting operations.

SUMMARY OF THE INVENTION

In one aspect, the present invention provides an apparatus for folding a web. The apparatus includes a first conveyor, a second conveyor in close proximity to the first conveyor, a folding wheel aligned in close proximity to both the first and second conveyors, and a folding bar extending above and generally parallel with the second conveyor.

In various embodiments, the first and second conveyors may define an included angle of 15 to 40 degrees. In various embodiments, the apparatus may further include a folding board located proximate to the second conveyor such that the folding bar extends between the folding board and the second conveyor. In some embodiments, the folding wheel may include a shaft and the folding bar may be connected to the shaft and cantilevered over the second conveyor. In some embodiments, the folding bar may be shaped like the number "7." In some embodiments, at least one of the first and second conveyors is a vacuum conveyor.

In another aspect, the present invention provides a method for folding a web. The method includes providing a web to a first conveyor, passing the web about a folding wheel to define a folded edge, transferring the web to a second conveyor, and folding the web about a folding bar to maintain the folded edge.

In some embodiments, the first conveyor and the second conveyor may define an included angle of 15 to 40 degrees. In some embodiments, the web includes a series of cut outs and the folded edge extends through the series of cut outs. The series of cut outs define a series of bridging portions located between the cut outs. The method further includes spanning at least one cut out with the folding bar and contacting at least two bridging portions contemporaneously with the folding bar to maintain the folded edge after the web exits the folding wheel. The method further includes spanning at least two cut outs with the folding bar and contacting at least three bridging portions contemporaneously with the folding bar to maintain the folded edge after the web exits the folding wheel. The method further includes spanning at least three cut outs with the folding bar and contacting at least four bridging portions contemporaneously with the folding bar to maintain the folded edge after the web exits the folding wheel.

In some embodiments, the web may further include a plurality of absorbent cores joined thereto, wherein the absorbent cores at least partially overlay the cut outs. In some embodiments, the method further includes joining a first laminate web with a second laminate web. In some embodiments, both the first and the second laminate webs comprise the cut outs. In some embodiments, the web is directed to the folding bar with a folding board to maintain the folded edge between the folding bar and the folding board.

In another aspect, the present invention provides another method for folding a web. The method includes providing a web to a first conveyor, the web comprising a series of cut outs, the series of cut outs defining bridging portions located between the cut outs. The method further includes folding the web about a folding wheel to define a folded edge, wherein the folded edge extends through the series of cut outs. The method further includes transferring the web to a second conveyor, the first and second conveyors defining an included angle of 15 to 40 degrees. The method further includes folding the web about a folding bar to maintain the folded edge, and spanning at least one cut out with the folding bar and contemporaneously contacting at least two bridge portions to maintain the folded edge of the web about the folding bar.

In various embodiments, the method may further include spanning at least two cut outs with the folding bar and contacting at least three bridging portions with the folding bar to maintain the folded edge. The method may further include joining a plurality of absorbent cores to the web. The method may further include a first laminate web joined with a second laminate web wherein both of the laminate webs comprise the series of cut outs. In various embodiments, the method may further include directing the web about the folding bar with a folding board to maintain the folded edge between the folding bar and the folding board.

The above-mentioned and other aspects of the present invention will become more apparent, and the invention itself will be better understood by reference to the drawings and the following description of the drawings.

BRIEF DESCRIPTION OF THE DRAWINGS

Corresponding reference characters indicate corresponding parts throughout the drawings.

DEFINITIONS

Figure 1:
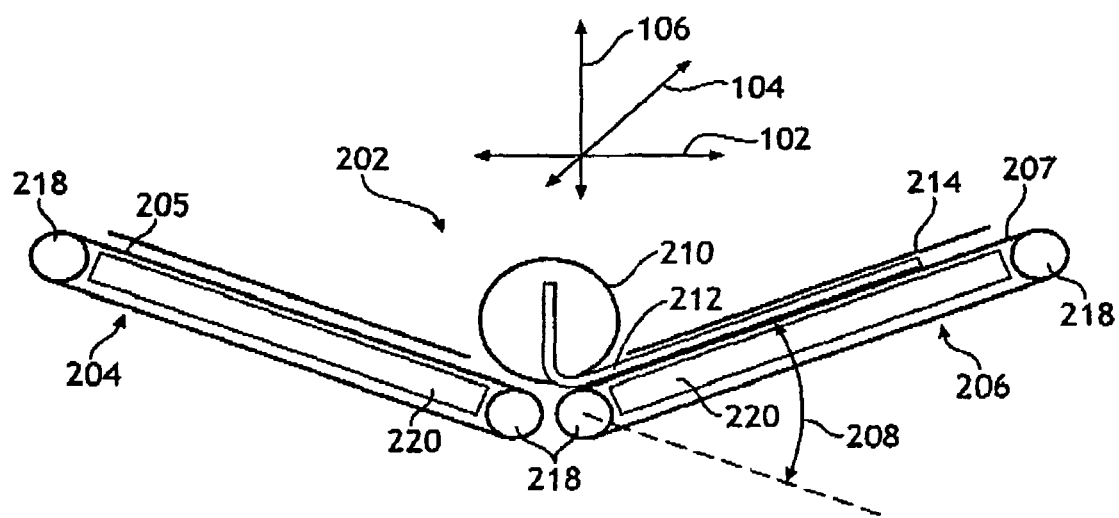
FIG. 1 representatively illustrates a side schematic view of an exemplary apparatus of the present invention.

Within the context of this specification, each term or phrase below will include the following meaning or meanings.

"Attach" and its derivatives refer to the joining, adhering, connecting, bonding, sewing together, or the like, of two elements. Two elements will be considered to be attached together when they are integral with one another or attached directly to one another or indirectly to one another, such as when each is directly attached to intermediate elements. "Attach" and its derivatives include permanent, releasable, or refastenable attachment. In addition, the attachment can be completed either during the manufacturing process or by the end user.

"Bond" and its derivatives refer to the joining, adhering, connecting, attaching, sewing together, or the like, of two elements. Two elements will be considered to be bonded together when they are bonded directly to one another or indirectly to one another, such as when each is directly bonded to intermediate elements. "Bond" and its derivatives include permanent, releasable, or refastenable bonding.

"Boxer shorts" or "Shorts" refers to pants, trunks, briefs, and the like, and include garments that may be relatively loose fitting or snug at the leg area.

"Complex web" refers to a continuous web of material having one or more layers or "plies" wherein the one or more layers may be joined at least partially together by any suitable means. A complex web may further include a plurality of discrete absorbent assemblies attached intermittently thereto. A complex web may further include one or more cut away portions. A complex web may include two layers of material bonded together at a crotch seam surrounding a crotch opening with a plurality of discrete absorbent assemblies attached thereto.

"Connect" and its derivatives refer to the joining, adhering, bonding, attaching, sewing together, or the like, of two elements. Two elements will be considered to be connected together when they are connected directly to one another or indirectly to one another, such as when each is directly connected to intermediate elements. "Connect" and its derivatives include permanent, releasable, or refastenable connection. In addition, the connecting can be completed either during the manufacturing process or by the end user.

"Disposable" refers to articles which are designed to be discarded after a limited use rather than being laundered or otherwise restored for reuse.

The terms "disposed on," "disposed along," or "disposed toward" and variations thereof are intended to mean that one element can be integral with another element, or that one element can be a separate structure bonded to or placed with or placed near another element.

"Downstream" refers to the positioning of one element or event further in the direction of material travel relative to another element or event in a process.

"Elastic," "elasticized," "elasticity," and "elastomeric" mean that property of a material or composite by virtue of which it tends to recover its original size and shape after removal of a force causing a deformation. Suitably, an elastic material or composite can be elongated by at least 25 percent (to 125 percent) of its relaxed length and will recover, upon release of the applied force, at least 10 percent of its elongation. Desirably an elastic material or composite may be elongated by at least 100 percent (to 200 percent), more desirably by at least 300 percent (to 400 percent), of its relaxed length and recover, upon release of an applied force, at least 50 percent of its elongation.

"Fabrics" is used to refer to all woven, knitted and non-woven fibrous webs.

"Front-to-back crotch seam" refers to a seam extending from the front region to the back region of a pant-style garment, through the crotch region. The seam can join two separate pieces of material, or separate edges of a single piece of material.

"Garment shell" refers to those portions of the articles produced by the process of the present invention that are not part of the absorbent assembly.

"Hanging legs" refers to the characteristic of a garment intended to be worn about the lower torso where the garment includes material that extends below the crotch of the garment and is intended to generally cover at least a portion of the leg of the wearer; the material may be loose fitting about the leg of the wearer, fit snugly about the leg of the wearer and/or may be elastic or non-elastic.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90 degrees are designated "wettable" or hydrophilic, while fibers having contact angles greater than 90 degrees are designated "nonwettable" or hydrophobic.

"Layer" when used in the singular can have the dual meaning of a single element or a plurality of elements.

"Liquid impermeable", when used in describing a layer or multi-layer laminate, means that a liquid, such as urine, will not pass through the layer or laminate, under ordinary use conditions, in a direction generally perpendicular to the plane of the layer or laminate at the point of liquid contact.

"Machine direction" refers to the direction in which material travels during a production process, as opposed to "cross machine direction" which refers to the direction that is generally transverse and perpendicular to the machine direction.

"Nonwoven" and "nonwoven web" refer to materials and webs of material that are formed without the aid of a textile weaving or knitting process.

"Open Configuration" refers to the condition that the garment shell web is in before the formation of a waist opening and a pair of leg openings in the article. The garment shell web may be manipulated, have portions directed in the machine direction or the cross machine direction, or may be separated into individual garment chassis and still be in an open configuration, provided that the formation of the waist opening and the leg openings has not yet been completed.

"Overlap" refers to the condition where one element is positioned to be at least partially covering another element either directly or indirectly. It should be noted that one element may be beneath the other element and still be overlapping the other element.

"Pants" includes full length and short pants.

"Stretchable" means that a material can be stretched, without breaking, by at least 25 percent (to 125 percent of its initial (unstretched) length) in at least one direction, suitably by at least 100 percent (to 200 percent of its initial length), desirably by at least 150 percent (to at least 250 percent of its initial length).

"Upstream" refers to the positioning of an element or event further in the direction opposite to the direction of material travel relative to another element or event in a process.

These terms may be defined with additional language in the remaining portions of the specification.

DETAILED DESCRIPTION

Figure 2:
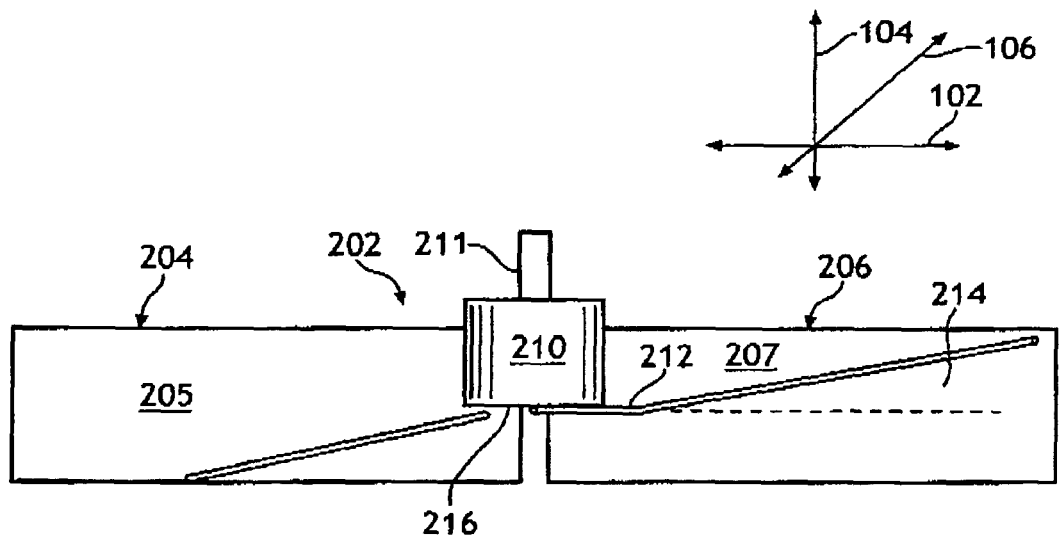
FIG. 2 representatively illustrates a top schematic view of the apparatus of FIG. 1.

Referring now to FIGS. 1 and 2, an apparatus for folding a complex web is shown at reference numeral 202. FIG. 1 representatively illustrates a side perspective view of the apparatus 202. FIG. 2 representatively illustrates a top perspective view of the apparatus 202. The apparatus 202 has a machine direction 102, a cross machine direction 104, and an orthogonal direction 106. The apparatus 202 includes a first conveyor 204 and a second conveyor 206. The first conveyor 204 and the second conveyor 206 define an included angle 208 as illustrated in FIG. 1. The first conveyor 204 and the second conveyor 206 may be generally aligned in the cross machine direction 104 as illustrated in FIG. 2. The apparatus 202 further includes a folding wheel 210 and a folding bar 212. In some embodiments, the apparatus 202 may further include a folding board 214.

The apparatus 202 can include any suitable web conveyors, such as, for example, conveyor belts, vacuum drums, transport rolls, electromagnetic suspension conveyors, fluid suspension conveyors, or the like, and combinations thereof. As representatively shown, the web conveyors 204 and 206 can be provided by endless conveyor belts 205 and 207 disposed about rollers 218. One or more of the rollers 218 may be driven by any suitable means, such as, for example, an electric motor to move the conveyor belts 205 and 207 in the machine direction 102.

In a particular configuration of the invention, a vacuum suction box 220 can be located below the first conveyor belt 205 and/or the second conveyor belt 207 to assist in transporting a web through the apparatus 202. The vacuum boxes 220 may open onto the belts 205 and 207 and suction air out of the vacuum boxes to draw air flow through the perforations in the conveyor belts 205 and 207. This air flow may in turn operate to draw the web to the conveyor belts 205 and 207. The air flow in conjunction with the moving conveyor belts 205 and 207 may be configured to transport the web through the apparatus 202.

The first conveyor 204 and the second conveyor 206 define an included angle 208 as illustrated in FIG. 1. The included angle 208 can suitably range from 0 to 50 degrees, 10 to 45 degrees, and 15 to 40 degrees.

The folding wheel 210 may be positioned proximate both the first conveyor 202 and the second conveyor 204 as illustrated in FIGS. 1 and 2. The folding wheel 210 may be rotatably mounted to a shaft 211. The shaft 211 may extend through the folding wheel 210 and may be supported on both ends or may be cantilevered from one end as illustrated in FIG. 2. The shaft 211 and the folding wheel 210 may be operatively rotated by any suitable drive mechanism, such as an electrical motor (not shown). In some embodiments, the shaft 211 and/or the folding wheel 210 may not be driven and may be allowed to freely rotate.

The folding wheel 210 defines a folding wheel edge 216. The folding wheel 210 and the folding wheel edge 216 may be positioned in the cross machine direction 104 at any suitable position relative to the first conveyor 204 and the second conveyor 206. As illustrated in FIG. 2, the folding wheel edge 216 may be positioned approximately at the cross directional 104 centerline of the first conveyor 204 and the second conveyor 206.

The folding bar 212 is cantilevered over the second conveyor 206 and is generally parallel to the second conveyor belt 207 and is supported by any suitable means such that a continuous web may pass between the folding bar 212 and the second conveyor 206 and may be folded over the folding bar 212. In some embodiments, the folding bar 212 may be joined to non-rotating bracketry associated with the folding wheel 210. In some embodiments, the folding bar 212 may be shaped like the number "7" and may extend approximately to the point on the folding wheel 210 closest to the second conveyor belt 207 as illustrated in FIG. 1.

In various embodiments, the apparatus 202 may further include one or more folding boards 214. In the illustrated embodiment of FIGS. 1 and 2, the folding board 214 is positioned in a generally facing relation with the second conveyor belt 207. The folding board 214 may be positioned at an angle as compared with the second conveyor belt 207. The folding board 214 may be positioned such that the folding bar 212 extends between the folding board 214 and the second conveyor belt 207.

Figure 3:
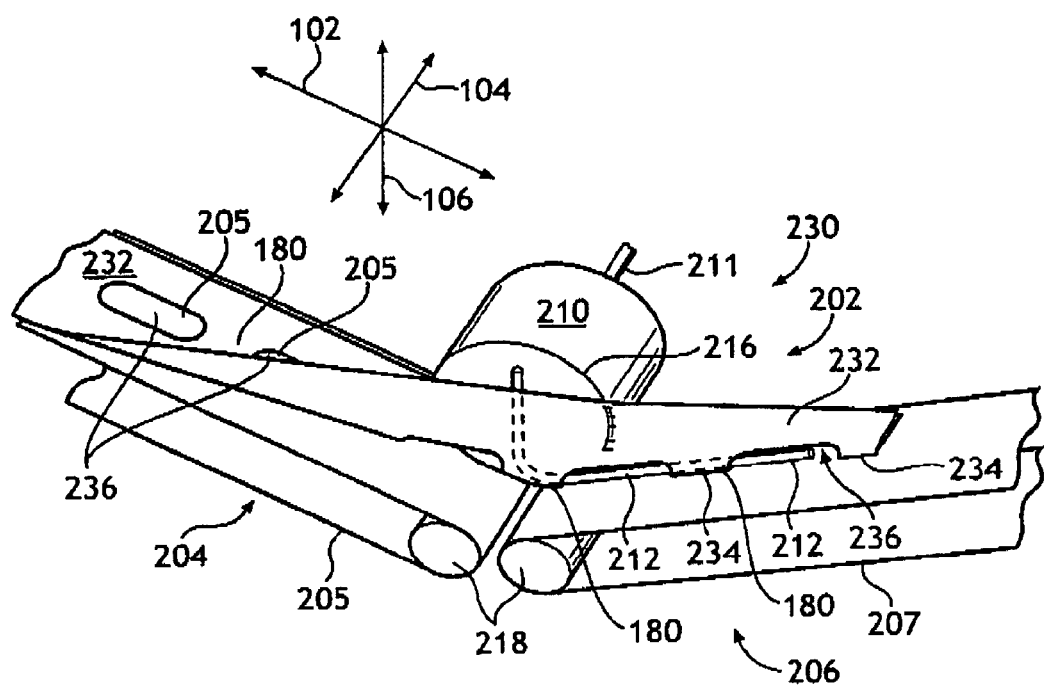
FIG. 3 representatively illustrates a perspective view of an exemplary method and apparatus of the present invention.
Figure 4:
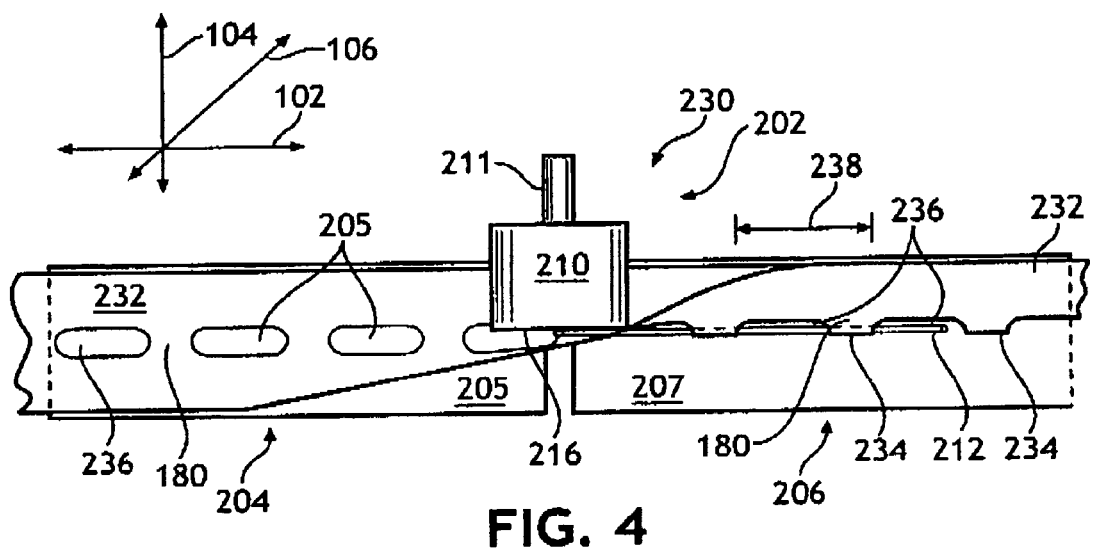
FIG. 4 representatively illustrates a top view of the method and apparatus of FIG. 3.

Referring now to FIGS. 3 and 4, the apparatus 202 of FIGS. 1 and 2 is illustrated as part of a method 230 for folding a web 232. FIG. 3 representatively illustrates a side perspective view of the method 230 whereas FIG. 4 representatively illustrates the method 230 of FIG. 3 from a top view. The method 230 includes providing a web 232 to the first conveyor 204 and passing the web 232 about the folding wheel 210. The web 232 folds about the folding wheel edge 216 to define a folded edge 234 in the web 232. The method 230 further includes transferring the web 232 to the second conveyor 206 wherein the first conveyor 204 and the second conveyor 206 define an included angle 208 of 15 to 40 degrees. Finally, the method 230 includes folding the folded edge 234 of the web 232 about the folding bar 212 to maintain the folded edge 234 as the web is moved away from the folding wheel 210.

In various embodiments, the method 230 may include folding a web 230 having a plurality of cut away portions 236 wherein the folded edge 234 extends through the cut away portions 236 as representatively illustrated in FIGS. 3 and 4. In some embodiments the cut away portions 236 have a repeat length 238. The repeat length 238 is the length from the front of a first cut away portion 236 to the front of a second consecutive cut away portion 236 as illustrated in FIG. 4. In some embodiments, the method 230 includes maintaining the folded edge 234 of the web 232 about the folding bar 212 for a distance of at least 2, at least 3, at least 4, or at least 5 times the repeat length 238.

The web 230 of FIGS. 3 and 4 includes a bridging portion 180 spanning between the cut out portions 236. The folding bar 212 of the present invention allows the folded edge 234 to be maintained even in sections including a cut away portion 236 by maintaining contact with the bridging portions 180. In other words, the web 230 folds about the folding wheel edge 216 to define the folded edge 234 when a bridging portion 180 is in contact with the folding wheel 210. When a cut away portion 236 moves past the folding wheel edge 216, the folded edge 216 is not lost because the folding bar 212 extends from the folding wheel 210 and maintains contact with one or more of the bridging portions 180. As will be apparent to one skilled in the art, the folded edge 234 is therefore only truly an "edge" in the bridging portions 180 and merely defines the position of the web 230 relative to the folding wheel edge 216 in the cut away portions 236.

In some embodiments, the method 230 further includes folding a web 232 having a plurality of absorbent cores joined thereto. In some embodiments, the absorbent cores may at least partially overlay the cut away portions 236.

In some embodiments, the method 230 includes folding a web 232 wherein the web 232 includes a first web attached with a second web to form a laminate web. One of more of the laminate webs may include cut away portions.

In some embodiments, the method 230 includes directing the web 232 about the folding bar 212 with a folding board 214 to maintain the folded edge 234.

The method and apparatus of the present invention may be utilized in any suitable converting operation. One particularly useful application includes folding a complex web as part of a garment manufacturing operation. For example, the present method and apparatus may be suitable for folding the complex web described in U.S. Application 2005/0241748, entitled "Process For Making A Garment Including An Absorbent Assembly," published on Nov. 3, 2005 to Allen, the entirety of which is incorporated herein by reference to the extent it is consistent (i.e., not in conflict) herewith.

Figure 5:
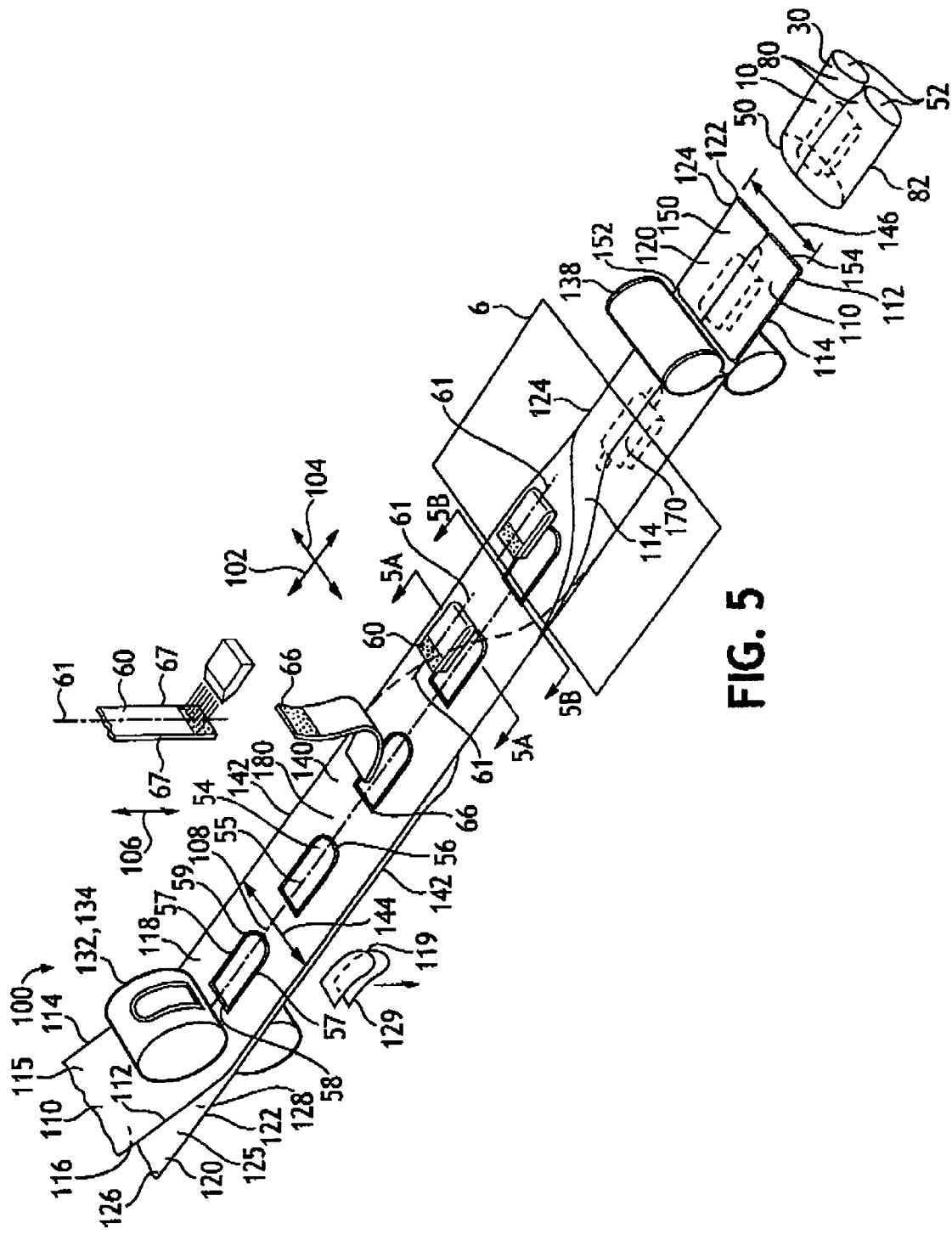
FIG. 5 representatively illustrates an exemplary garment manufacturing process incorporating one aspect of the method and apparatus of the present invention.

Referring now to FIG. 5, a process for making garments to be worn about the lower torso is shown in its entirety at reference numeral 100 and includes the method and apparatus described above. The process 100 will be described in terms of making boxer shorts, or shorts 10, but it should be readily recognized that the process of the present invention may be equally applicable with pants, trunks, briefs, and other garments that may be worn about the lower torso and having a waist opening, a pair of leg openings, and optionally a pair of hanging legs. The shorts 10 of the present invention can include a garment shell and may further include an absorbent assembly 60, as will be described in greater detail below. Such garments and a process for making them, are described in U.S. Pat. No. 6,192,521 issued Feb. 27, 2001 to Alberts, et al., the disclosure of which is incorporated herein by reference to the extent it is consistent (i.e., not in conflict) herewith.

The process 100 of the various aspects of the present invention defines a machine direction indicated at the arrow marked 102, and a cross machine direction indicated at the arrow marked 104 that is perpendicular to the machine direction 102. The process 100 also defines an orthogonal direction, indicated at the arrow marked 106 that is perpendicular to the plane created by the machine direction 102 and the cross machine direction 104. Further, the process also defines a process centerline 108 extending in the machine direction 102.

In some aspects, the process 100 is represented with the orthogonal direction 106 being generally vertical in orientation. Nonetheless, as can be readily appreciated by those of skill in the art, the orthogonal direction 106 of the present invention may also be generally horizontal in orientation or may otherwise be oriented and still be within the scope of the present invention.

The process includes transporting a garment shell web 140 in the machine direction 102. The garment shell web 140 can include any combination of materials that together provide the garment shell of the shorts 10. The garment shell web 140 may be provided by a single web or a plurality of webs. For example, the garment shell web 140 can include a first web 110 and a second web 120. Thus, the first web 110 and the second web 120 may be provided and transported in the machine direction 102 to provide the garment shell web 140. In addition, the garment shell web 140 defines a pair of opposed garment shell web side edges 142 that extend substantially in the machine direction 102 and a garment shell web width 144 in the cross machine direction 104.

In yet another alternative, it may be noted that the first web 110 and the second web 120 may be provided by separate webs or may alternatively be provided by a single web that is folded about the machine direction 102 and then subsequently separated (not shown). As representatively illustrated in FIG. 5, the webs 110 and 120 can be provided in a substantially superposed relationship with each other.

The first web 110 of the garment shell web 140 defines a first web first edge 112 and a first web second edge 114 that is opposite the first web first edge 112, and a first web interior 115 located within the first web first edge 112 and the first web second edge 114. The first web 110 also defines a first web inner surface 116 that is in facing relationship with the second web 120, and a first web outer surface 118 that is opposite the first web inner surface 116.

The second web 120 of the garment shell web 140 defines a second web first edge 122 and a second web second edge 124 that is opposite the second web first edge 122, and a second web interior 125 that is located within the second web first edge 122 and the second web second edge 124. The second web 120 also defines a second web inner surface 126 that is in facing relationship with the first web 110, and a second web outer surface 128 that is opposite the second web inner surface 126.

As representatively illustrated in FIG. 5, the webs 110 and 120 may be provided in at least a partially facing relationship, and may be in a substantially completely facing relationship. For example, the second web inner surface 126 may be in at least a partially facing relationship with the first web inner surface 116. It should be noted that the first and second web inner and outer surfaces 116, 118, 126, and 128 need not correspond to a body facing surface 28 and an exterior surface 30 of a resultant garment when the garment is produced.

The process 100 is illustrated in FIG. 5 as being configured to have the garment shell web 140 pass through the process 100 in a generally horizontal orientation. Nonetheless, as can be readily appreciated by those of skill in the art, the process 100 may be configured to have the garment shell web 140 pass through the process 100 in a generally vertical or other orientation and still be within the scope of the present invention. Suitably, the garment shell web 140 can be initially provided to the process 100 in a generally planar position. For example, in configurations where the garment shell web 140 is provided by a first web 110 and a second web 120, the webs 110 and 120 may initially be provided to the process 100 with the web edges 112, 114 and 122, 124 in a spaced relationship.

The garment shell web 140 may be any suitable fabric to provide the shorts 10. In particular, the garment shell web 140 may suitably be of materials which are comfortable against the skin and non-irritating. Since it is contemplated that the shorts 10 can be either disposable or durable (i.e., launderable), both nonwoven and woven materials are contemplated for the garment shell web 140. For example, the garment shell web 140 can be selected from a wide variety of materials, including elastic, stretchable, or nonstretchable materials. Any other type of nonwoven laminate or woven or knitted fabric known to those skilled in the art can also be used. The garment shell web 140 can be a single layer of material or a multi-layered laminate structure. Moreover, as discussed above, the garment shell web 140 may be provided by a plurality of webs (e.g., the webs 110 and 120).

The garment shell web 140 may be provided to and transported through the process 100 by various methods as are known in the art. For example, the garment shell web 140 may be unwound and drawn through the process 100 via driven rolls, belt conveyors, chain conveyors, and the like, or combinations thereof (not shown).

In the various aspects of the process 100 of the present invention, the garment shell web 140 may also include a crotch seam 56. The garment shell web 140 may be provided to the process 100 with the crotch seam 56 already in place, or the crotch seam 56 may by incorporated in the garment shell web 140 in the course of the process 100.

For example, as representatively illustrated in FIG. 5, the garment shell web 140 includes webs 110 and 120, which may be attached to one another to provide a crotch seam 56. In particular aspects, spaced portions of the garment shell web 140 may be attached to one another at selected locations to provide a plurality of crotch seams 56. The seams 56 may be substantially continuous, or may be provided by a series of intermittent bonds. The crotch seam 56 may be of various shapes to produce the desired result. For example, the crotch seam 56 may be generally rectilinear, curvilinear (for example, circular or oval), generally "D" shaped, or generally "U" shaped. In particular aspects, the crotch seam 56 may be at least partially curvilinear to provide a garment with improved fit and comfort.

The crotch seam 56 may be imparted to the garment shell web 140 by a bonding device 132 in various ways as are known in the art. For example, the crotch seam 56 may be formed by bonding portions of the garment shell web 140 (e.g., bonding the first web 110 to the second web 120) as it travels in the machine direction 102. This bonding can be accomplished by using ultrasonic, pressure, or thermal bonding wheels rotating in a facing relationship to form the crotch seam 56. For example, an anvil wheel and a horn wheel defining a nip can be used to form the crotch seam 56. Alternatively, any suitable bonding method known in the art can be used, such as adhesives, sewing or the like.

The process 100 of the present invention may further include providing a crotch opening 54 in the garment shell web 140. For example, portions of the garment shell web 140 may be removed by the process 100 in order to provide the crotch opening 54. Alternatively, the garment shell web 140 may be provided to the process 100 with a crotch opening 54 or a series of crotch openings 54 already in place. In a particular aspect, the process 100 of the present invention may include selectively removing portions of the garment shell web 140 to provide a series of spaced crotch openings 54. Suitably, the boundaries of the crotch opening 54 may be located completely within the garment shell web side edges 142. The crotch openings 54 may be separated by bridging portions 180.

In a particular aspect, as representatively illustrated in FIG. 5, the garment shell web 140 is provided by webs 110 and 120. The process 100 may include selectively removing a portion of the first web 110 to define a first web removal portion 119. In addition, the process 100 of the present invention may include selectively removing a portion of the second web 120 to define a second web removal portion 129. As mentioned above, the portions of the webs 110 and 120 that are removed 119 and 129 can be located within the first web interior 115 and the second web interior 125. Suitably, when the garment shell web 140 includes multiple layers of material, the portions that are removed 119 and 129 are generally aligned to define a crotch opening 54 that passes through the garment shell web 140. For instance, as illustrated in FIG. 5, the portions of the webs 110 and 120 that are removed 119 and 129 are generally in alignment with each other, and as such, define a common crotch opening 54 within the first web interior 115 and within the second web interior 125.

The crotch opening 54 may be any suitable shape to provide a crotch gap in the garment shell of the shorts 10. For example, the crotch opening 54 may be rectangular, oval shaped, curvilinear, rectilinear, and the like, or combinations thereof. In particular, as representatively illustrated in FIG. 5, the crotch opening 54 may be elongated in the machine direction 102 and may be at least partially curvilinear. The crotch opening 54 can define a pair of side edges 57 that generally extend in the machine direction 102. The crotch opening 54 may also define an opening centerline 55 extending in the machine direction 102.

Further, the crotch opening 54 may also define a pair of end edges. For instance, the crotch opening 54 can define an upstream end edge 58 and a downstream end edge 59 opposite the upstream opening end edge 58, each generally extending in the cross machine direction 104. Suitably, at least one of the upstream or downstream end edges 58 and 59 are curvilinear, and still more suitably, both of the end edges 58 and 59 are curvilinear. Alternatively, one of the upstream or downstream opening end edges 58 and 59 may be substantially parallel with the cross machine direction 104 while the other opening end edge 58 or 59 is curvilinear.

The crotch opening 54 may suitably be located proximate the process centerline 108. For example, the opening centerline 55 may be adjacent and parallel to the process centerline 108. In particular embodiments, the opening centerline 55 may overlap the process centerline 108. Alternatively, the opening centerline 55 may be offset in the cross machine direction 104 from the process centerline 108. In such a configuration, the shorts 10 may be tailored to provide a greater amount of crotch depth in a front region 22 of the shorts 10 or in a back region 24 of the shorts 10.

The providing of the crotch opening 54 may be accomplished by various methods as are known in the art. For example, a portion or portions of the garment shell web 140 may be removed by a cutting device 134 such as cutting rolls, a die cutting assembly, a water cutting device or an ultrasonic cutter, or combinations thereof. Alternatively, other suitable cutting methods known in the art can be used. In yet another alternative, portions of the garment shell web 140 may be perforated and may be removed subsequently in the process 100 to provide the crotch opening 54.

It should be noted that the step of providing the crotch seam 56 and the step of providing of the crotch opening 54 need not occur in a particular order, and moreover, need not happen sequentially. For example, the step of providing of a crotch opening 54 may occur prior to the formation of a crotch seam 56 or the step of forming a crotch seam 56 may occur prior to providing the crotch opening 54. In yet another alternative, the formation of the crotch seam 56 may occur at the same time as the formation of the crotch opening 54. For instance, this may be accomplished by utilizing an ultrasonic bonder that is also capable of cutting.

As can be readily appreciated, the crotch opening 54 and the crotch seam 56 may be located as necessary in the garment shell web 140, and may suitably be positioned proximate one another in the garment shell web 140, or be otherwise associated. For example, as representatively illustrated in FIG. 5, the crotch seam 56 may be located adjacent the crotch opening 54. In addition, as representatively illustrated in FIG. 5, the crotch seam 56 may partially or fully circumscribe the crotch opening 54.

In addition, and as will be discussed in greater detail below, the garment shell web may be separated into individual garment chassis 150. This separation may occur such that a crotch seam 56 and an associated crotch opening 54 may be divided by the step of separation into a pair of associated crotch seams 56 and crotch openings 54, with one crotch seam 56 and one crotch opening 54 being associated with the garment chassis 150.

In the various aspects of the present invention, the process 100 may include disposing an absorbent assembly 60 on the garment shell web 140. The absorbent assembly 60 can be any structure which is generally compressible, conformable, non-irritating to the skin, and capable of absorbing and retaining liquids and certain body wastes. The absorbent assembly 60 can be manufactured in a wide variety of sizes and shapes, from a wide variety of liquid absorbent materials commonly used in the art, and may be stretchable, non-stretchable, or elastic. For example, the absorbent assembly 60 can suitably include a matrix of hydrophilic fibers, such as a web of cellulosic fluff, mixed with particles of a high-absorbency material commonly known as superabsorbent material.

For example, as representatively illustrated in FIG. 5, an absorbent assembly 60 may be disposed on the garment shell web 140 proximate the crotch opening 54. In particular, where the garment shell web 140 is provided by a first and second web 110 and 120, the absorbent assembly 60 may be disposed on at least one of the webs 110 and 120. For example, as representatively illustrated in FIG. 5, the absorbent assembly 60 may suitably be disposed on the first web 110 proximate the crotch opening 54.

The absorbent assembly 60 may be disposed on the garment shell web 140 at various points throughout the process 100 as can be appreciated by one of skill in the art. Suitably, the absorbent assembly 60 may be disposed on the garment shell web 140 while the garment shell web is in an open configuration. That is, the garment shell web 140 may be in a completely planar position and still be in an open configuration. Further, as will be discussed in greater detail below, portions of the garment shell web 140 may be directed in the machine direction 102 or the cross machine direction 104, and the garment shell web 140 is still in the open configuration. Thus, provided that portions of the garment shell web 140 have not been attached together to form a waist opening 50 and a pair of leg openings 52, the garment shell web 140 is in an open configuration. In a particular aspect, and as representatively illustrated in FIG. 5, the garment shell web 140 is provided by a first web and a second web 110 and 120. In such a configuration, the absorbent assembly 60 can be disposed on at least one of the webs 110 and 120 while the edges 112, 114 and 122, 124 of at least one of the webs 110 and 120 are in a spaced relationship, and therefore the garment shell web 140 is in an open configuration.

The absorbent assembly 60 of the present invention may also define an absorbent assembly centerline 61 that, upon being disposed upon the garment shell web 140, extends in the machine direction 102. Suitably, when an absorbent assembly 60 is disposed on the garment shell web 140, the absorbent assembly centerline 61 may be located proximate one of the opening side edges 57 (FIG. 5). In such an arrangement, the absorbent assembly 60 may overlap at least a portion of the crotch opening 54. More suitably, the absorbent assembly centerline 61 may be located adjacent one of the opening side edges 57 and be parallel or generally parallel with the process centerline 108.

The absorbent assembly 60 may be arranged on the garment shell web 140 in a number of ways, as may be influenced by the configuration of the absorbent assembly 60 and the style of the shorts 10. For example, as representatively illustrated in FIG. 5, a single absorbent assembly 60 may be associated with each crotch opening 54 prior to the garment shell web 140 being separated into individual garment chassis 150. In such a configuration, upon separation of the garment shell web 140 into individual garment chassis 150, both the opening 54 and the absorbent assembly 60 may also be divided into a pair of openings 54 and a pair of absorbent assemblies 60, with one of the pair of crotch openings 54 and one of the pair of absorbent assemblies 60 being associated with the garment chassis 150.

The process 100 of the various aspects of the present invention may also include directing at least a portion of the garment shell web 140 in the cross machine direction 104 to define a folded portion. Moreover, the folded portion may define an overlapping portion, such as a first web overlapping portion and/or a second web overlapping portion. As will be discussed in greater detail below, the directing of at least a portion of the garment shell web 140 in the cross machine direction 104 may occur before or after the garment shell web 140 is separated into individual garment chassis 150.

Figure 5A:
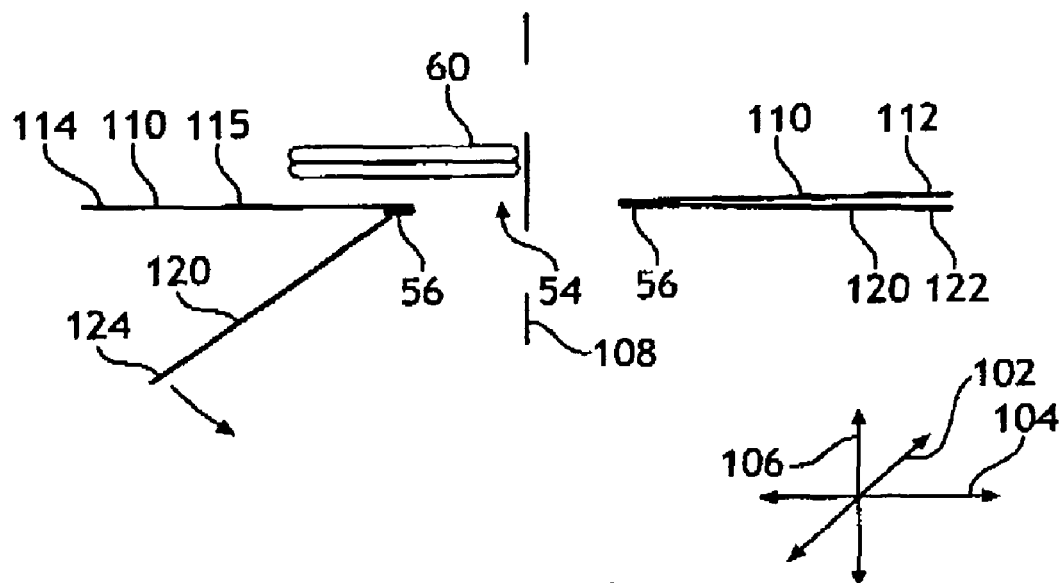
FIG. 5A representatively illustrates a cross sectional view of the method and apparatus of FIG. 5 taken along the line 5A-5A.
Figure 5B:
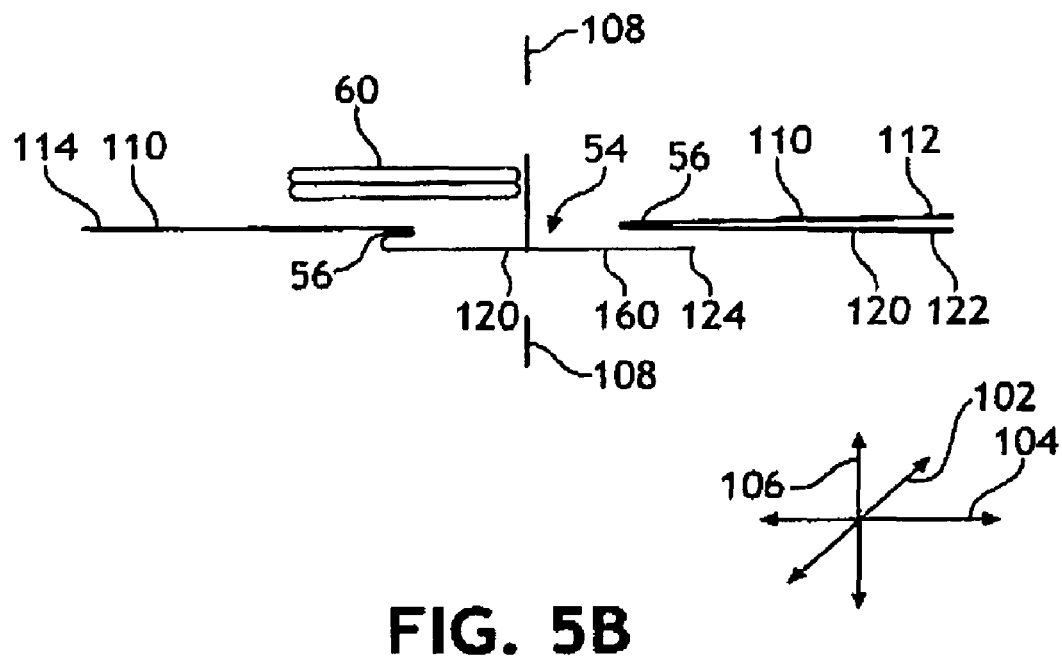
FIG. 5B representatively illustrates a cross sectional view of the method and apparatus of FIG. 5 taken along the line 5B-5B.

For example, in one aspect and as representatively illustrated in FIG. 5A, the second web 120 may be directed in the cross machine direction 104 to define a folded portion. FIG. 5A representatively illustrates a cross sectional view of the method and apparatus of FIG. 5 taken along the line 5A-5A. Similarly, FIG. 5B representatively illustrates a cross sectional view of the method and apparatus of FIG. 5 taken along the line 5B-5B. Suitably, a portion of the second web 120 proximate to either the second web first edge 122 or the second web second edge 124 is directed in the cross machine direction 104 toward the process centerline 108 and the opposing edge 122 or 124 such that the folded portion at least partially overlaps the crotch opening 54 to define a second web overlapping portion 160. For example, the second web overlapping portion 160 may overlap the entire crotch opening 54, as illustrated in FIG. 5B, or alternatively the second web overlapping portion 160 may overlap only part of the crotch opening 54. In yet another alternative, a portion of the second web 120 may be directed in the cross machine direction 104 such that the second web overlapping portion 160 overlaps substantially the entire crotch opening 54 and the second web first edge 122 is substantially adjacent the second web second edge 124.

Thus, to direct a portion of the second web 120 in the cross machine direction 104, the second web 120 may be folded upon itself starting from the second web first edge 122. As a result, that portion of the second web 120 may be folded upon itself proximate the crotch seam 56 toward the process centerline 108 and the second web second edge 124 and desirably at least partially overlaps the crotch opening 54. Alternatively, in another aspect, a portion of the second web 120 may be folded upon itself starting from the second web second edge 124 as illustrated in FIGS. 5A and 5B. As a result, that portion of the second web 120 is folded upon itself proximate the crotch seam 56 toward the process centerline 108 and the second web first edge 122 and desirably at least partially overlaps the crotch opening 54.

To provide the second web overlapping portion 160, the second web 120 is suitably directed in the cross machine direction 104 and folded upon itself from the second web edge 122 or 124 that is closer to the intended location of the absorbent assembly 60 (whether it has yet been disposed on the webs 110 or 120 or not), relative to the other second web edge 122 or 124.

For example, as representatively illustrated in FIG. 5A, the second web second edge 124 is proximate the location of the absorbent assembly 60 (disposed on the first web 110). Accordingly, the second web second edge 124 is included in the portion of the second web 120 that is directed in the cross machine direction 104 toward the process centerline 108 and the second web first edge 122 to at least partially overlap the crotch opening 54.

The directing of the second web 120 in the cross machine direction 104 to define a folded portion can occur either before or after the absorbent assembly 60 is disposed upon the webs 110 and 120. In arrangements where the directing of the second web 120 occurs after the absorbent assembly 60 is disposed on one of the webs 110 or 120, the second web overlapping portion 160 may also overlap at least a portion of the absorbent assembly 60. That is, as representatively illustrated in FIGS. 5B and 7A, the portion of the second web 120 directed in the cross machine direction 104 may overlap the crotch opening 54 and overlap the absorbent assembly 60 to define a folded portion and the second web overlapping portion 160.

Figure 6:
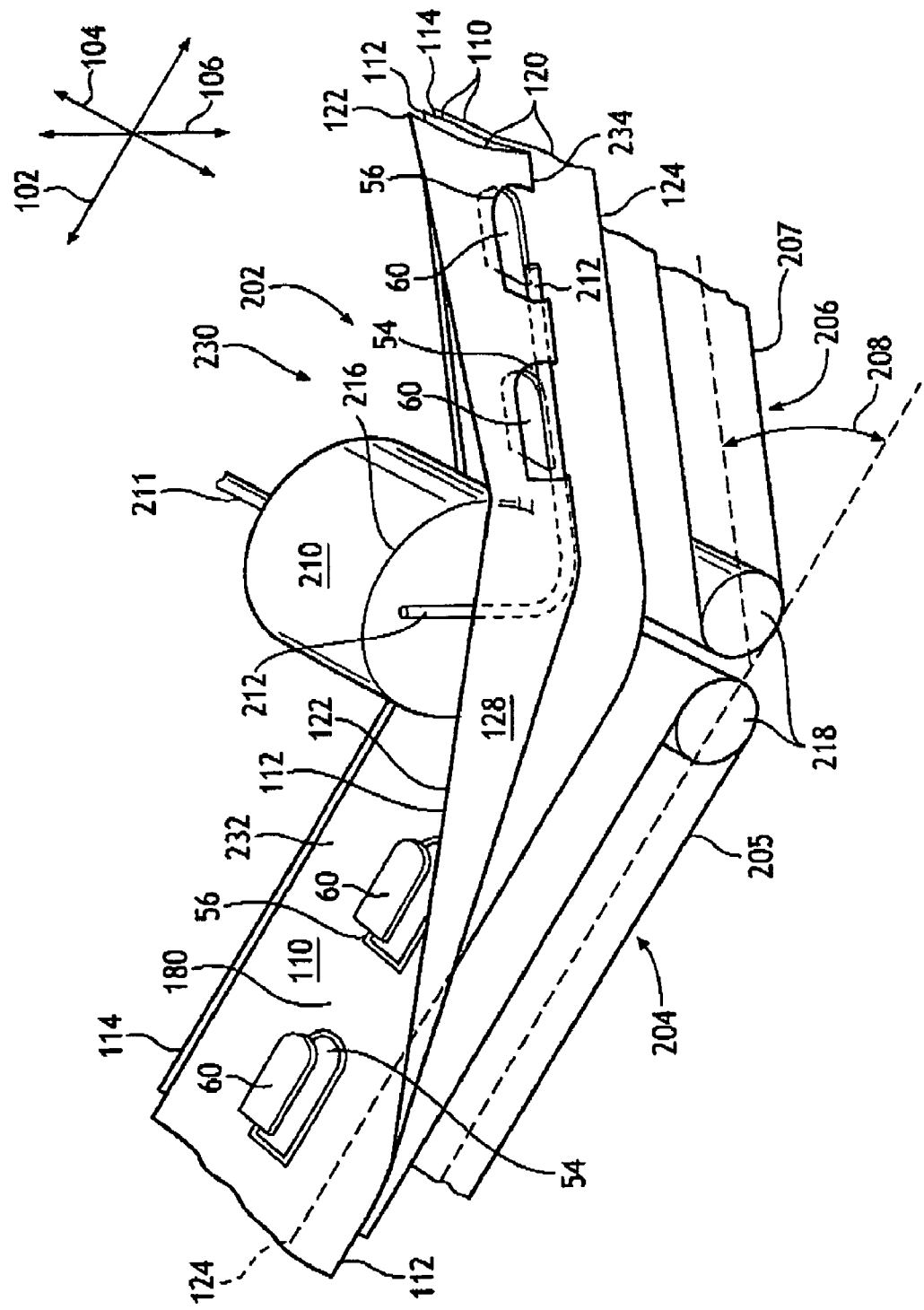
FIG. 6 representatively illustrates a detailed view of the portion of the method and apparatus of FIG. 5 designated by box 6.
Figure 7:
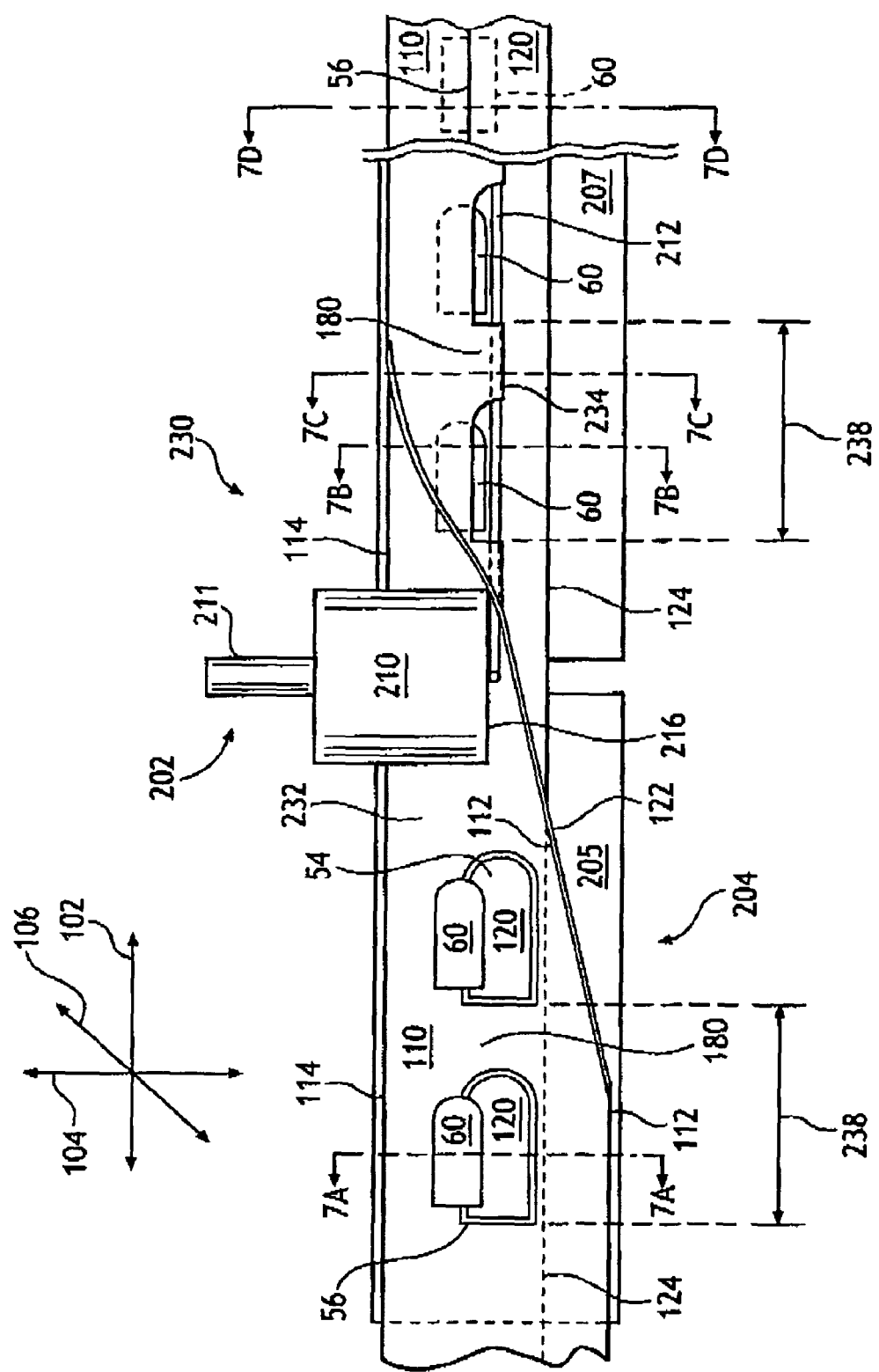
FIG. 7 representatively illustrates a top view of the method and apparatus of FIG. 6.

Further, the process 100 of the various aspects of the present invention may also include directing at least a portion of the first web 110 in the cross machine direction 104 to define a folded portion as representatively illustrated in FIG. 6. FIG. 6 representatively illustrates, in greater detail, the portion of the method and apparatus of FIG. 5 circumscribed by box 6. FIG. 7 representatively illustrates a top view of the method and apparatus of FIG. 6. FIGS. 7A, 7B, 7C, and 7D representatively illustrate cross sectional views of the method and apparatus of FIG. 7 taken along the lines 7A-7A, 7B-7B, 7C-7C, and 7D-7D respectively.

Suitably, the first web 110 is directed in the cross machine direction 104 such that the folded portion of the first web 110 at least partially overlaps the absorbent assembly 60 to define a first web overlapping portion 170. For example, the first web overlapping portion 170 may overlap the absorbent assembly 60 entirely, or alternatively, the first web overlapping portion 170 may overlap a portion of the absorbent assembly 60. In addition, subsequent to the directing of the first web 110, a portion of the absorbent assembly 60 may be overlapped by the first web overlapping portion 170 and a portion of the second web 120 as representatively illustrated in FIG. 7B.

Figure 7A:
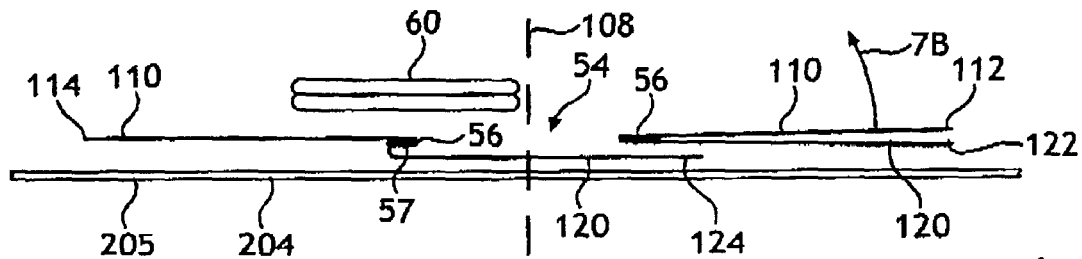
FIGS. 7A, 7B, 7C, and 7D representatively illustrate cross sectional views of the method and apparatus of FIG. 7 taken along the lines 7A-7A, 7B-7B, 7C-7C, and 7D-7D respectively.
Figure 7B:
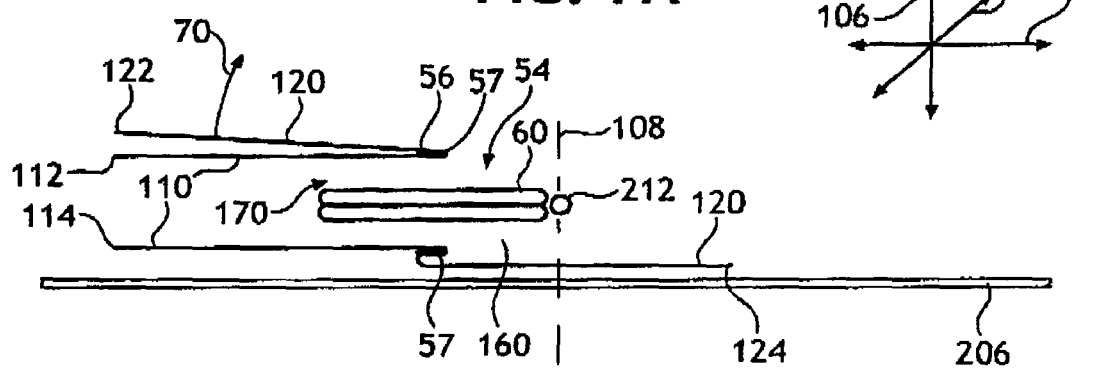

In particular aspects, portions of the first web 110 proximate to either the first web first edge 112 or the first web second edge 114 may be directed in the cross machine direction 104 toward the process centerline 108 and the opposing edge 112 or 114. Thus, the first web 110 may be folded upon itself from the first web first edge 112 or the first web second edge 114. As a result, in one aspect, the portion of the first web 110 that is proximate the first web first edge 112 can be directed in the cross machine direction 104 toward the process centerline 108 and the first web second edge 114, and at least partially overlap the absorbent assembly 60. Further, the portion of the first web 110 that is proximate the first web first edge 112 can be directed in the cross machine direction 104 such that the first web first edge 112 is substantially adjacent to the first web second edge 114 as illustrated in FIG. 7B.

Alternatively, in another aspect, the portion of the first web 110 that is proximate the first web second edge 114 can be directed in the cross machine direction 104 toward the process centerline 108 and the first web first edge 112, and at least partially overlap the absorbent assembly 60. Further, the portion of the first web 110 that is proximate the first web second edge 114 can be directed in the cross machine direction 104 such that the first web second edge 114 is substantially adjacent to the first web first edge 112.

As discussed previously, the various webs are moved about the folded edge 234 as representatively illustrated in FIGS. 6 and 7. The folded edge 234 is defined by the folding wheel 210 and in particular the folding wheel edge 216. As the web 232 moves past the folding wheel edge 216 the web 232 is folded along the folded edge 234. However, as the crotch openings 54 pass the folding wheel edge 216 there is no material to define and maintain the folded edge 234. In order to prevent the loss of the folded edge 234, the folding bar 212 extends from the folding wheel 210 and essentially "extends" the folding wheel edge 216 in the machine direction 102 a sufficient distance to span at least one crotch opening 54. By "extending" the folding wheel edge 216 via the folding bar 212, the bridging portions 180 of the web 232 remain in contact with the folding bar 212. Therefore, even when a crotch opening 54 passes the folding wheel edge 216, portions of the folded edge 234 remain in contact with the folding bar 212 via the bridging portions 180 as representatively illustrated in FIGS. 7 and 7C.

Figure 7C:
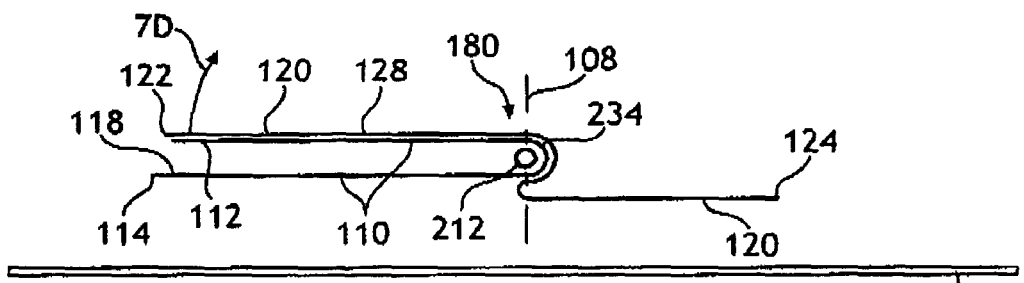

The folding bar 214 may extend any suitable distance beyond the folding wheel edge 216. As described previously, the web 232 defines a multiplicity of repeat lengths 238. The folding bar 214 may extend one, two, three, or more repeat lengths 238 such that the folding bar 214 may be in contemporaneous contact with one, two, three, or more bridging portions 180. As such, the folding bar 214 may maintain the folded edge 234 until the web 232 is completely folded as illustrated in FIG. 7C. FIG. 7C provides a cross sectional view of a bridging portion 180 wherein the folded edge 234 contacts the folding bar 212 to maintain the folded edge 234 even as a crotch opening 54 passes the folding wheel edge 216.

In particular aspects, in order to define a folded portion and provide the first web overlapping portion 170, the first web 110 may suitably be directed in the cross machine direction 104 and folded upon itself from the first web edge 112 or 114 that is distant from the absorbent assembly 60 relative to the opposing edge 112 or 114. For example, as illustrated in FIG. 7A, the first web first edge 112 is distant from the location of the absorbent assembly 60 (disposed on the first web 110) relative to the first web second edge 114 and is included in the portion of the second web 120 that is directed in the cross machine direction 104 to partially overlap the absorbent assembly 60. Moreover, the first web first edge 112 is placed substantially adjacent said first web second edge 114 as representatively illustrated in FIGS. 7B and 7C. In addition, the opening side edges 57 may become substantially aligned in the orthogonal direction 106 as a result, as representatively illustrated in FIG. 7B.

Figure 7D:
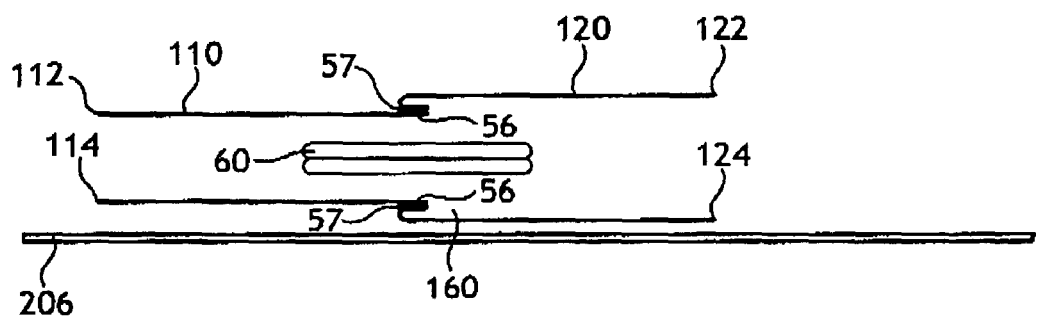

Referring now to FIGS. 7B and 7C, the second web first edge 122 is directed in the cross machine direction 104 such that the second web first edge 122 is substantially aligned with the second web second edge 124 as representatively illustrated in FIG. 7D.

The directing of the first web 110 and the second web 120 need not happen in any particular order. For example, the directing of the first web 110 may occur before the directing of the second web 120, or vice versa. In addition, as indicated above, the directing of the first web 110 and the second web 120 may occur before or after the garment shell web 140 is separated into individual garment chassis 150. Moreover, the directing of the webs may, but need not occur consecutively; for example, intervening steps may occur between the directing of the webs 110 and 120. Nonetheless, in configurations where the steps of directing the first web 110 and the second web 120 have occurred in the process 100, the edges 112, 114, 122, and 124 of the webs 110 and 120 can become substantially aligned as a result.

For example, as representatively illustrated in FIG. 7D, upon the directing of the first web 110 and the second web 120 in the cross machine direction 104 as described above, the first web first edge 112 and the first web second edge 114 can be arranged to be substantially adjacent each other. Similarly, following the directing of the first web 110 and the second web 120 in the cross machine direction 104 as described above, the second web first edge 122 and the second web second edge 124 may be arranged to be substantially adjacent each other.

The process 100 of the present invention may also include the step of attaching a portion of the absorbent assembly 60 to the garment shell web 140 by a variety of methods as are known in the art. For example, the absorbent assembly 60 may be attached by adhesives, ultrasonic bonding, pressure bonding, sewing, and the like, or combinations thereof.

As mentioned above, the process 100 may further include the step of separating the garment shell web 140 into a plurality of discrete individual sections or garment chassis 150. The separation of the garment shell web 140 into individual garment chassis 150 may occur at various points in the process 100. For example, the separation before or after the crotch opening 54 is provided in the garment shell web 140, before or after disposing the absorbent assembly 60 on the garment shell web 140, and before or after portions of the garment shell web 140 are directed in the cross machine direction 104.

The garment shell web 140 may be separated into garment chassis 150 in a variety of ways as are known in the art. For example, the process 100 may include a separation device 138 that cuts the garment shell web 140 into individual garment chassis 150. Specifically the separation device 138 may be a die cutter, a water cutter, a rotary cutter, an ultrasonic cutter, or the like.

Portions of the garment shell web 140 may be arranged and attached together to form a waist opening and a pair of leg openings 52 and to provide the shorts 10. For example, portions of the webs 110 and 120 may be attached together as representatively illustrated in FIG. 5. In particular, the first web first edge 112 may be attached to the first web second edge 114. Similarly, the second web first edge 122 may be attached to the second web second edge 124. Accordingly, shorts 10 with a waist opening 50, a pair of leg openings 52, and optionally a pair of hanging legs 80 may be provided by the process 100. In addition, in such a configuration, upon attaching the web edges 112, 114, 122, and 124 together, the webs 110 and 120 may define a garment web width 146 in the cross machine direction 104 that is less than the garment shell web width 144.

In a particular aspect, the attaching of the first web first edge 112 to the first web second edge 114 and the second web first edge 122 to the second web second edge 124 can form a pair of side seams 82. The side seams 82 can take any number of forms, including both refastenable and non-refastenable seams as is known in the art.

Optionally, the process 100 may be configured to provide the shorts 10 such that the webs 110 and 120 may be attached together at a different time and/or location in order to form a pair of side seams 82 and a waist opening 50 and a pair of leg openings 52. That is, the process 100 may be configured to provide an intermediate garment element where the attaching of the first web first edge 112 to the first web second edge 114 and the attaching of the second web first edge 122 to the second web second edge 124 are completed at another location or by the end user. In particular, the edges 112, 114, 122, and 124 may include complementary fasteners, such as hook and loop fasteners, so that the webs 110 and 120 may be attached together at a later time. In such an arrangement, the shorts 10 may, for example, be packaged with the edges 112, 114, 122, and 124 unattached so that the end user may attach the webs 110 and 120 and obtain a customized fit.

The process 100 may further include attaching waist elastic material 70 (FIG. 8) to the garment shell web 140. Suitably, the waist elastic material may be attached to the garment shell web 140 while the garment shell web is in an open configuration, or more suitably, in a planar configuration. For example, a portion of waist elastic material 70 may be attached to the first web 110 and a separate portion of waist elastic material 70 may be attached to the second web 120. The waist elastic material 70 may be attached to the webs 110 and 120 in a variety of locations. The waist elastic material 70 can be formed of any suitable elastic material including sheets, strands or ribbons of natural rubber, synthetic rubber, or thermoplastic elastomeric polymers.

The absorbent assembly 60 can also incorporate other materials that are designed primarily to receive, temporarily store, and/or transport liquid along the mutually facing surface with absorbent assembly 60, thereby maximizing the absorbent capacity of the absorbent assembly. One suitable material is referred to as a surge layer (not shown) and includes a material having a basis weight of about 50 to about 120 grams per square meter (gsm), and including a through-air-bonded-carded web of a homogenous blend of 60 percent 3 denier type T-256 bicomponent fiber including a polyester core/polyethylene sheath and 40 percent 6 denier type T-295 polyester fiber, both commercially available from Kosa Corporation of Salisbury, N.C. U.S.A.

The absorbent assembly 60 may also include a liner material that is intended to face the wearer in use. The liner can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like.

The absorbent assembly 60 may also include a suitable outercover intended to face away from the body of the wearer in use. The outercover desirably comprises a material that is substantially liquid impermeable. The outercover can be a single layer of liquid impermeable material, or may be a multi-layered laminate structure in which at least one of the layers is liquid impermeable. The liquid impermeable material can also be configured to permit vapors to escape from the interior of the absorbent body, while still preventing liquids from passing through the outercover.

In particular embodiments, the absorbent assembly 60 is thin to provide a slim, comfortable, non-bulky short 10. Any suitable thin absorbent assembly may be used, such as for example, the thin absorbent described in WO 02/49565, published Jun. 27, 2002, by Sawyer et al., the disclosure of which is incorporated herein by reference to the extent it is consistent (i.e., not in conflict) herewith.

The absorbent assembly 60 optionally may include a pair of containment flaps 62 (FIGS. 5 and 6) which are configured to provide a barrier to the transverse flow of body exudates. Suitable constructions and arrangements for the containment flaps 62 are generally well known to those skilled in the art and are described in U.S. Pat. No. 4,704,116 issued Nov. 3, 1987 to Enloe, which is incorporated herein by reference to the extent that it is consistent (i.e., not in conflict) herewith.

To further enhance containment and/or absorption of body exudates, the absorbent assembly 60 may also suitably include absorbent assembly waist elastics 68 and leg elastics 64, as are known to those skilled in the art (FIGS. 5 and 6). The absorbent assembly waist elastics 68 can be operatively joined to the outercover and/or the liner along the opposing absorbent assembly end edges 66. The leg elastics 64 can be operatively joined to the outercover and/or the liner along the opposite absorbent assembly side edges 67.

The absorbent assembly waist elastics 68 and the absorbent assembly leg elastics 64 can be formed of any suitable elastic material. As is well known to those skilled in the art, suitable elastic materials include sheets, strands or ribbons of natural rubber, synthetic rubber, or thermoplastic elastomeric polymers. In one particular aspect, for example, the leg elastics 64 can include a plurality of dry-spun coalesced multifilament spandex elastomeric threads sold under the trade name LYCRA® and available from E. I. Du Pont de Nemours and Company, Wilmington, Del., U.S.A.

Figure 8:
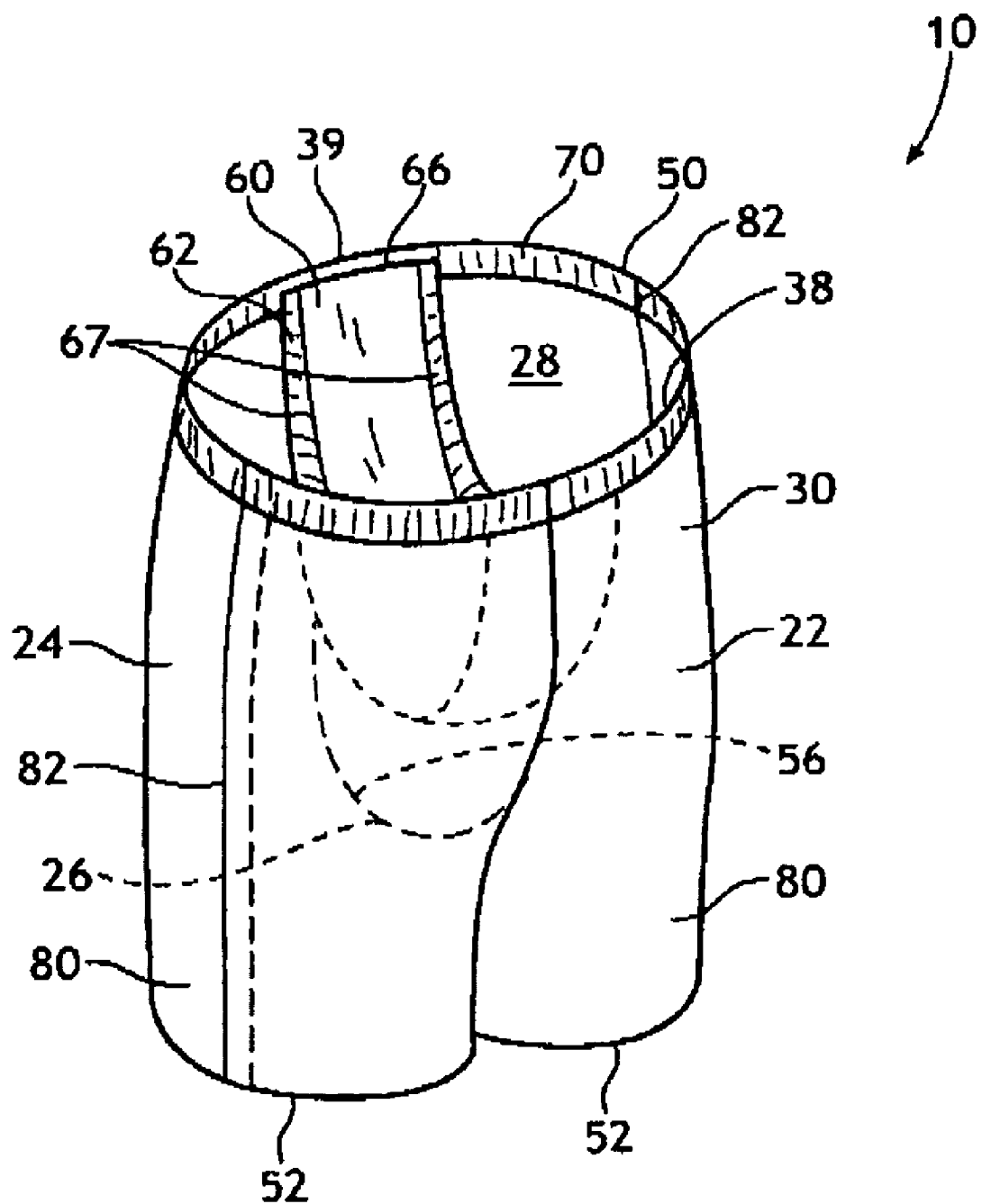
FIG. 8 representatively illustrates an exemplary absorbent article manufactured in part by the method and apparatus of the present invention.

As representatively illustrated in FIG. 8, an embodiment of a short 10 produced by the process 100 of the present invention can include a front region 22, a back region 24, a crotch region 26, a bodyfacing surface 28 which is configured to contact the wearer, and an exterior surface 30 opposite the bodyfacing surface 28 which is configured to face away from the surface of the wearer's body. The short 10 also defines a pair of opposed waist edges, which are designated front waist edge 38 and back waist edge 39. The front region 22 is contiguous with the front waist edge 38, and the back region 24 is contiguous with the back waist edge 39. The front region 22 includes the portion of the short 10 which, when worn, is positioned on the front of the wearer while the back region 24 includes the portion of the short 10 which, when worn, is positioned on the back of the wearer. The crotch region 26 of the short 10 includes the portion of the short which, when worn, is positioned between the legs of the wearer and covers the lower torso of the wearer.

As illustrated in FIG. 8, the front and back regions 22 and 24 are joined together at side seams 82 and the left and right sides of the short 10 are joined together at the crotch seam 56 to define a three-dimensional short configuration having a waist opening 50 and a pair of hanging legs 80 with leg openings 52. In particular aspects, the crotch seam 56 may follow a path which begins substantially at the front waist edge 38, extends through the crotch region 26, and terminates substantially at the back waist edge 39. In alternative embodiments, the crotch seam 56 can follow a path which begins below the front waist edge 38 on the front region 22 and terminates below the back waist edge 39 on the back region 24. As is known in the art, the crotch seam 56 can be an inward butt seam or a lap seam (not shown). In the alternative, the crotch seam 56 can be an outward butt seam.

In particular embodiments and as mentioned above, the short 10 can include an absorbent assembly 60. The absorbent assembly 60 can be attached to the short 10 at the front waist edge 38 and/or back waist edge 39, or at some point below the front waist edge 38 and/or the back waist edge 39 in the front region 22 and back region 24. Alternatively or additionally, the absorbent assembly 60 can be attached to the pant 10 in the crotch region 26.

As various changes could be made in the above constructions and methods, without departing from the scope of the invention, it is intended that all matter contained in the above description and shown in the accompanying drawings shall be interpreted as illustrative and not in a limiting sense.

When introducing elements of the invention or the preferred aspect(s) thereof, the articles "a", "an", "the" and "said" are intended to mean that there are one or more of the elements. The terms "comprising", "including" and "having" are intended to be inclusive and mean that there may be additional elements other than the listed elements.

The invention claimed is:

1. A method for folding a web, comprising:
   providing a web to a first conveyor wherein the web includes a series of cut outs which define a series of bridging portions located between the cut outs,
   passing the web about a folding wheel to define a folded edge wherein the folded edge extends through the series of cut outs in the machine direction,
   transferring the web to a second conveyor,
   folding the web about a folding bar to maintain the folded edge wherein the folding bar extends in the machine direction and spans at least one cut out and contemporaneously contacts at least two bridging portions.

2. The method of claim 1 wherein the first conveyor and the second conveyor define an included angle of 15 to 40 degrees.

3. The method of claim 1 wherein the method further includes spanning at least two cut outs with the folding bar and contacting at least three bridging portions contemporaneously with the folding bar to maintain the folded edge after the web exits the folding wheel.

4. The method of claim 3 wherein the method further includes spanning at least three cut outs with the folding bar and contacting at least four bridging portions contemporaneously with the folding bar to maintain the folded edge after the web exits the folding wheel.

5. The method of claim 1 wherein the web further includes a plurality of absorbent cores joined thereto, wherein the absorbent cores at least partially overlay the cut outs.

6. The method of claim 1 wherein the web further includes a first laminate web joined with a second laminate web and wherein both the first and the second laminate webs comprise the cut outs.

7. The method of claim 1 further comprising directing the web about the folding bar with a folding board to maintain the folded edge between the folding bar and the folding board.

8. A method for folding a web, comprising:
   providing a web to a first conveyor, the web comprising a series of cut outs, the series of cut outs defining bridging portions located between the cut outs,
   folding the web about a folding wheel to define a folded edge, wherein the folded edge extends in the machine direction through the series of cut outs,
   transferring the web to a second conveyor, the first and second conveyors defining an included angle of 15 to 40 degrees,
   folding the web about a folding bar extending in the machine direction to maintain the folded edge, and
   spanning at least one cut out with the folding bar and contemporaneously contacting at least two bridge portions with the folding bar to maintain the folded edge of the web about the folding bar.

9. The method of claim 8 wherein the method further includes spanning at least two cut outs with the folding bar and contemporaneously contacting at least two bridging portions with the folding bar to maintain the folded edge.

10. The method of claim 9 wherein the web further includes a plurality of absorbent cores joined thereto.

11. The method of claim 10 wherein the web further includes a first laminate web joined with a second laminate web and wherein both of the laminate webs comprise the series of cut outs.

12. The method of claim 11 further comprising directing the web about the folding bar with a folding board to maintain the folded edge between the folding bar and the folding board.

* * * * *